US00PP27145P3

(12) United States Plant Patent
Grosser

(10) Patent No.: US PP27,145 P3
(45) Date of Patent: Sep. 13, 2016

(54) SWEET ORANGE TREE NAMED 'N13-32'

(50) Latin Name: ***Citrus sinensis* L. Osbeck**
Varietal Denomination: N13-32

(71) Applicant: Florida Foundation Seed Producers, Inc., Marianna, FL (US)

(72) Inventor: Jude W. Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 93 days.

(21) Appl. No.: 14/121,946

(22) Filed: Nov. 5, 2014

(65) Prior Publication Data

US 2016/0128253 P1 May 5, 2016

(51) Int. Cl.
*A01H 5/08* (2006.01)

(52) U.S. Cl.
USPC ..... Plt./202

(58) Field of Classification Search
USPC ..... Plt./202
See application file for complete search history.

(56) References Cited

PUBLICATIONS

Grosser et al., "Protoplast fusion and citrus improvement," *Plant Breeding Reviews* 8:339-374, 1990.
Larkin et al., "Somaclonal variation—a novel source of variability from cell cultures for plant improvement," *Theoret Appl Genet* 60:197-214, 1981.
Grosser et al., "Somaclonal Variation in Sweet Orange: Practical Applications for Variety Improvement and Possible Causes," pp. 219-234, in: Kahn, I.H. (Ed.). Citrus Genetics, Breeding and Biotechnology. CAB International, 2007.

*Primary Examiner* — Annette Para
(74) *Attorney, Agent, or Firm* — Dentons US LLP

(57) ABSTRACT

'N13-32' is a new and distinct early season clone of 'Hamlin' sweet orange. Fruit of 'N13-32' exhibit improved juice color and typical or better soluble solids than the industry standard for processing. Fruit juice of 'N13-32' produced a juice color score higher than 36, which is the minimum color score requirement to produce "Grade A" juice.

5 Drawing Sheets

Latin name of the genus and species of the plant claimed: *Citrus sinensis* L. Osbeck.
Variety denomination: 'N13-32'.

BACKGROUND OF THE INVENTION

The present invention relates to a new and distinct early season clone of 'Hamlin' sweet orange with improved juice color and typical or better soluble solids for processing named 'N13-32'. 'N13-32' is a somaclone (protoclone, meaning regenerated from protoplasts) regenerated from protoplasts isolated from an embryogenic suspension culture of standard 'Hamlin' (*Citrus sinensis* L. Osbeck) in 1989. Somaclonal variation is defined as variability in plants regenerated from tissue culture that is either induced or uncovered by a tissue culture process. Most somaclonal variation is negative, but if enough plants are examined, positive changes can usually be recovered. Somaclonal variation has been a primary source of genetic variation in sweet orange exploited in citrus improvement programs (Grosser et al. 2007). Hamlin 'N13-32' is the first of three superior 'Hamlin' somaclones selected for release from more than 500 somaclones under evaluation. The first asexual reproduction of 'N13-32' involved grafting of the original 'N13-32' tree onto 'Swingle' citrumelo rootstock and planting in the *Citrus* Research and Education Center (CREC) North-40 Block 16 in 1991 in Lake Alfred, Fla. Vegetative budwood of 'N13-32' was subsequently cut from the tree and successfully grafted onto 'Swingle' in 2002 in Lake Alfred, Fla. The resulting tree is the only existing $2^{nd}$ generation tree of 'N13-32' and has demonstrated true-to typeness.

SUMMARY OF THE INVENTION

'N13-32' was one of three original 'Hamlin' somaclones selected for improved juice color with typical or better soluble solids, based on several years of juice quality data (Table 1). Selection of improved Hamlin clones has proven to be quite difficult due to extreme variability in clonal juice quality data from year to year (unlike 'Valencia'). Improved color of 'N13-32' was noticed during the first two years of fruiting (1995-1996). Of the three original 'Hamlin' somaclones evaluated, 'N13-32' was selected because it was the first of more than 500 clones evaluated that produced a juice color score higher than 36 in December fruit in a pasteurized juice sensory evaluation (Table 2). The minimum required color score for grade A juice is 36. Traditional clones of 'Hamlin', the predominant early season processing orange in Florida, generally produce juice with a color score of around 34, and require blending with other darker colored juice to reach grade A status. Thus, a higher colored clone provides many advantages to the growing NFC (not from concentrate) business. 'Hamlin' clone 'N13-32' is also maintaining tree health better than adjacent 'Hamlin' clones in the test block that is now being impacted by Huanglongbing (HLB) disease.

TABLE 1

Non-pasteurized juice data from Hamlin N13-32 and Hamlin control.

| Sample Date | Clone ID | lbs. solids | OJ color score |
|---|---|---|---|
| Dec. 27, 2000 | 'N13.32' | 4.98 | 34.1 |
| | Control | 6.10 | 33.4 |

TABLE 1-continued

Non-pasteurized juice data from Hamlin N13-32 and Hamlin control.

| Sample Date | Clone ID | lbs. solids | OJ color score |
|---|---|---|---|
| Dec. 01, 2005 | 'N13-32' | 5.25 | 34.2 |
| | Control | 5.31 | 33.4 |
| Nov. 28, 2007 | 'N13-32' | 6.16 | 35.5 |
| | Control | 4.75 | 34.2 |
| Dec. 15, 2008 | 'N13-32' | 5.33 | 36.7 |
| | Control | 6.47 | 36.1 |

Sample size: 50-70 fruits

TABLE 2

Pasteurized orange juice sensory data, analyzed Jan. 3, 2012.

| Sample ID | Brix Cor. | Acid % | Ratio | pH | OJ Color index | Sinking Pulp | Limonin ppm | Flavor Score |
|---|---|---|---|---|---|---|---|---|
| Hamlin 'T8-40' | 11.65 | 0.51 | 22.84 | 3.96 | 33.92 | 12 | 1.6 | 3.25 |
| Hamlin 'N16-23' | 13.84 | 0.69 | 20.06 | 3.72 | 32.51 | 14 | 1.1 | 3 |
| 'Vernia' | 11.68 | 0.62 | 18.84 | 3.8 | 36.15 | 14 | 3 | 3.25 |
| Hamlin 'N13-32' | 11.01 | 0.6 | 18.35 | 3.85 | 36.14 | 10 | 1.1 | 3.13 |
| Hamlin 'N14-10' | 11.64 | 0.57 | 20.42 | 3.88 | 32.95 | 12 | 2.2 | 3.31 |
| 'Valquarius' | 11.21 | 0.79 | 14.19 | 3.58 | 36.86 | 12 | 1.6 | 3.38 |
| 'Early Gold' | 12.25 | 0.49 | 25 | 4.11 | 35.27 | 14 | 3.2 | 3.56 |
| 'Rosa' | 12.64 | 0.44 | 28.73 | 4.14 | 33.16 | 16 | 2 | 3.5 |
| 'Branca' | 11.19 | 0.49 | 22.84 | 4.04 | 34.38 | 14 | 1 | 3.44 |
| 'Serra D'Agua' | 12.54 | 0.55 | 22.8 | 3.97 | 35.52 | 14 | 1.3 | 3.31 |
| 'Hamlin' control | 11.86 | 0.53 | 22.38 | 3.86 | 32.81 | 10 | 2.3 | 3.19 |

*Lower flavor scores indicate better flavor.

BRIEF DESCRIPTION OF THE DRAWINGS

'N13-32' is illustrated by the accompanying photographs, which show the tree's form, foliage and fruit. The colors shown are as true as can be reasonably obtained by conventional photographic procedures. The photographs are from the original tree (approximately 20 years of age).

DETAILED BOTANICAL DESCRIPTION

Figure 1:
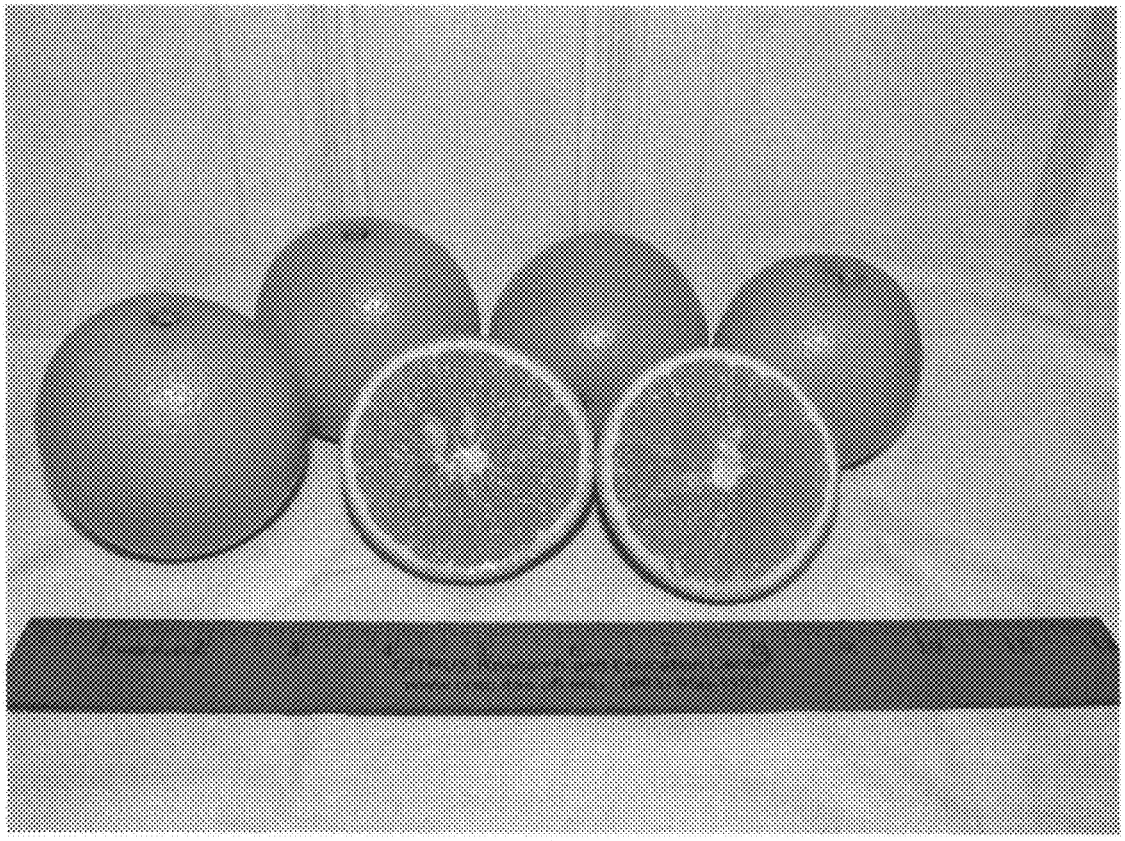
FIG. 1—Shows a close-up of the mature fruit with the rind and cross-sectional view of the fruit when cut in the center.
Figure 2:
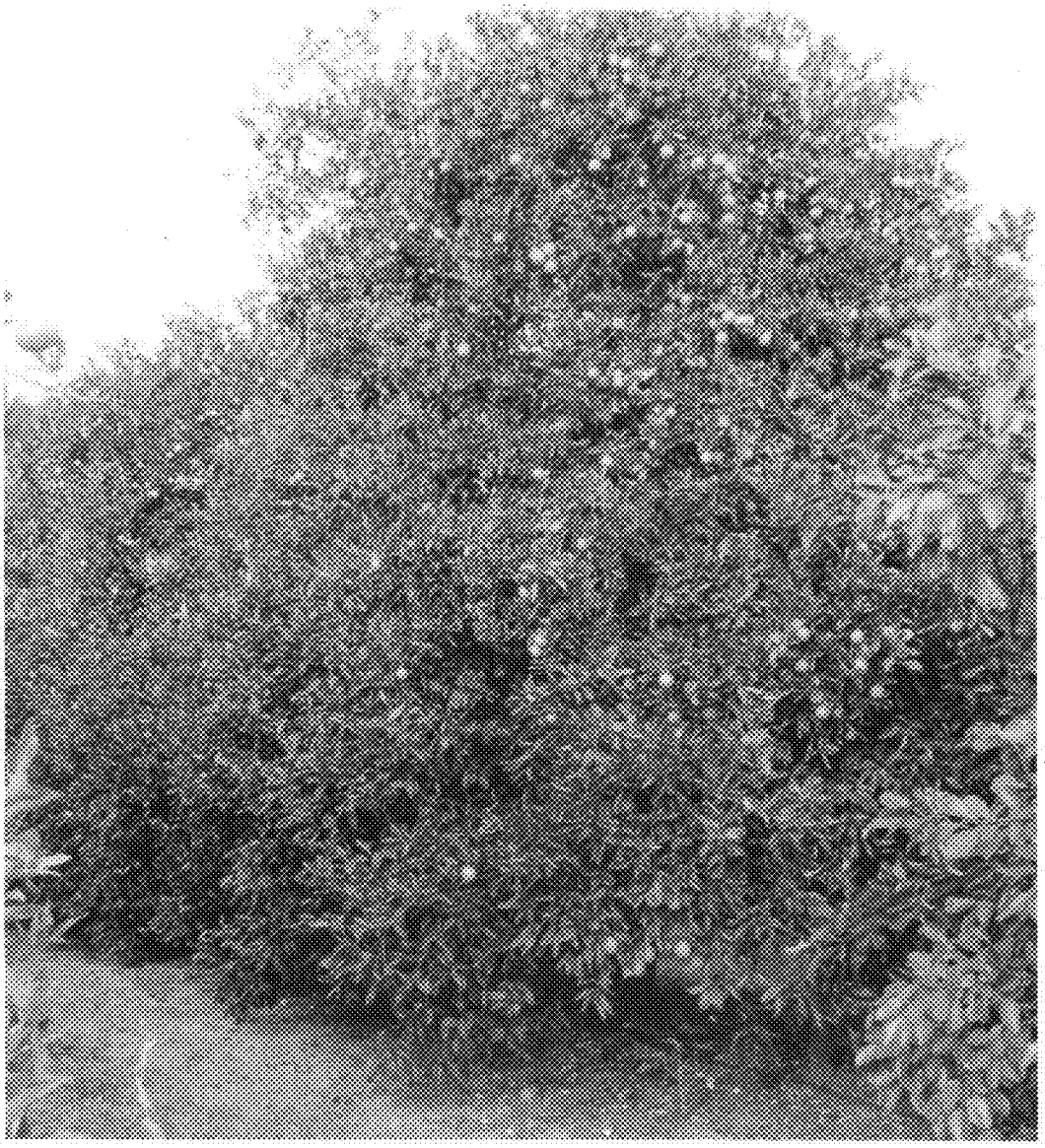
FIG. 2—Shows the original tree, in a block now impacted by HLB.
Figure 3:
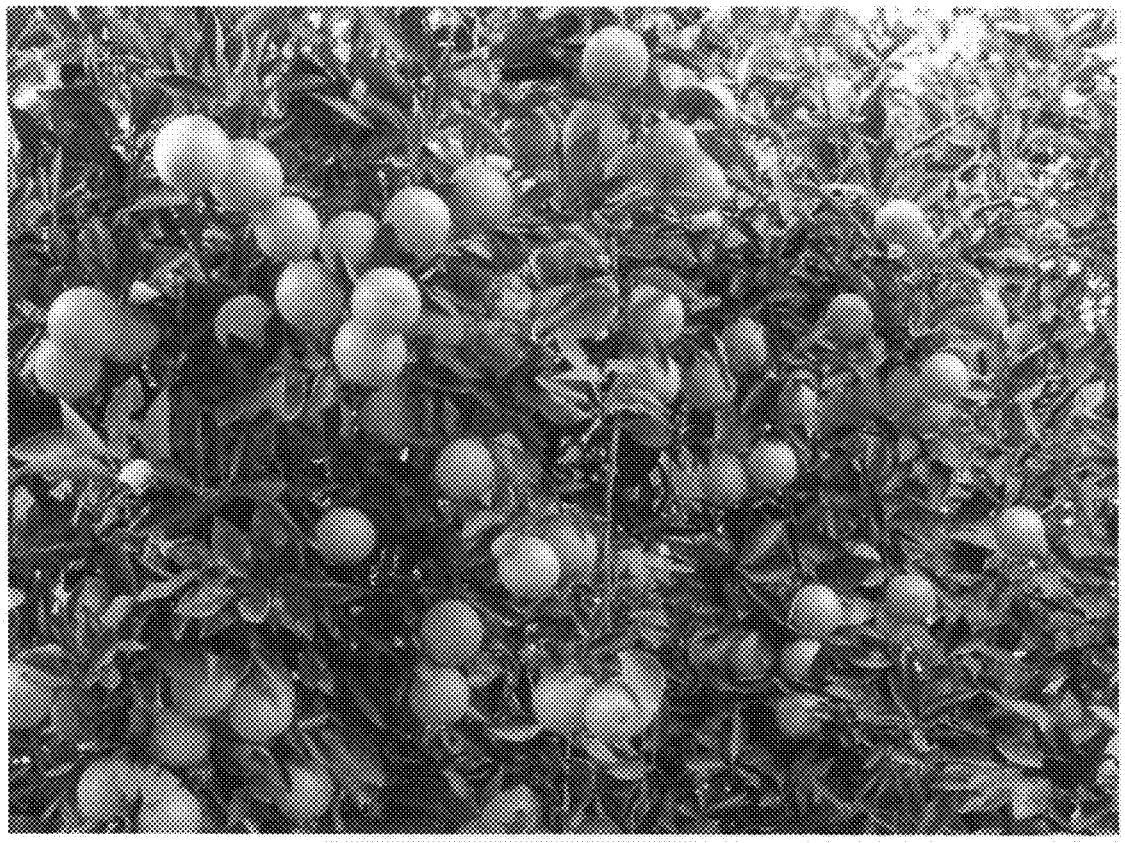
FIG. 3—Shows typical heavy cropping with of 'N13-32'.
Figure 4:
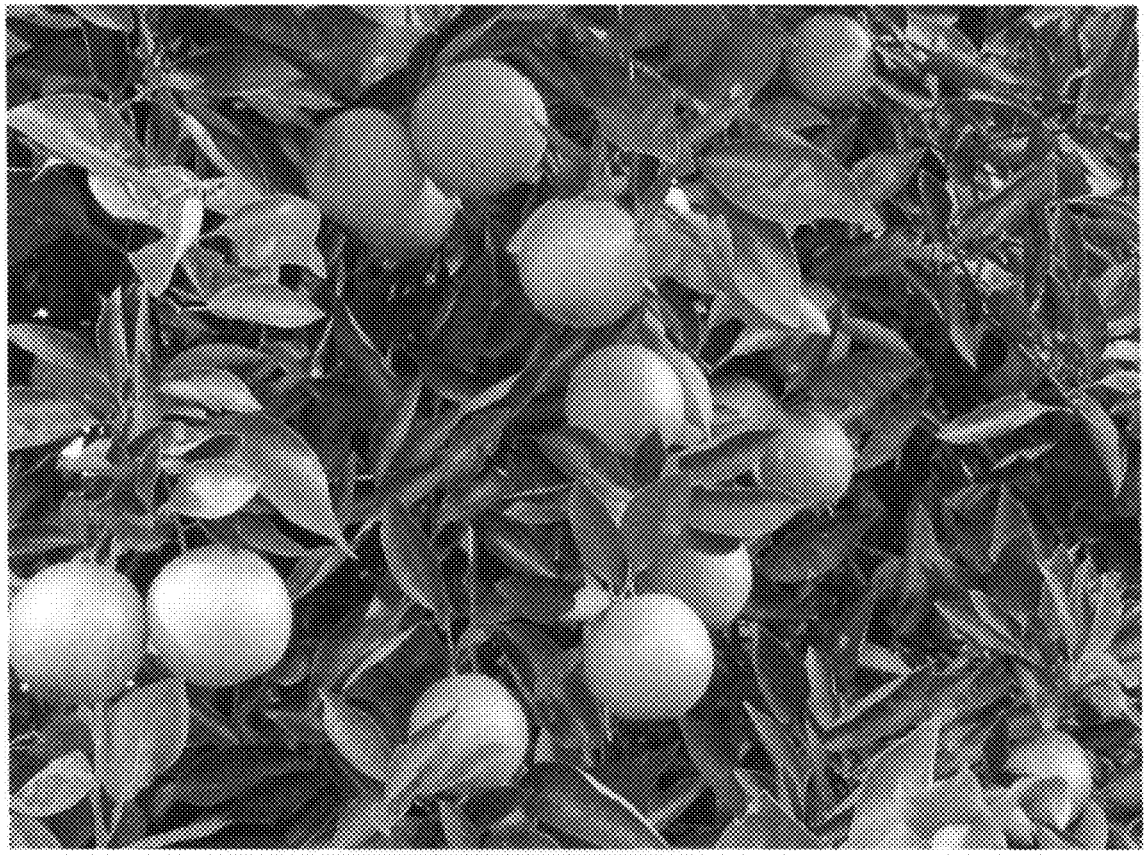
FIG. 4—Shows a close-up of leaves and mature fruit.
Figure 5:
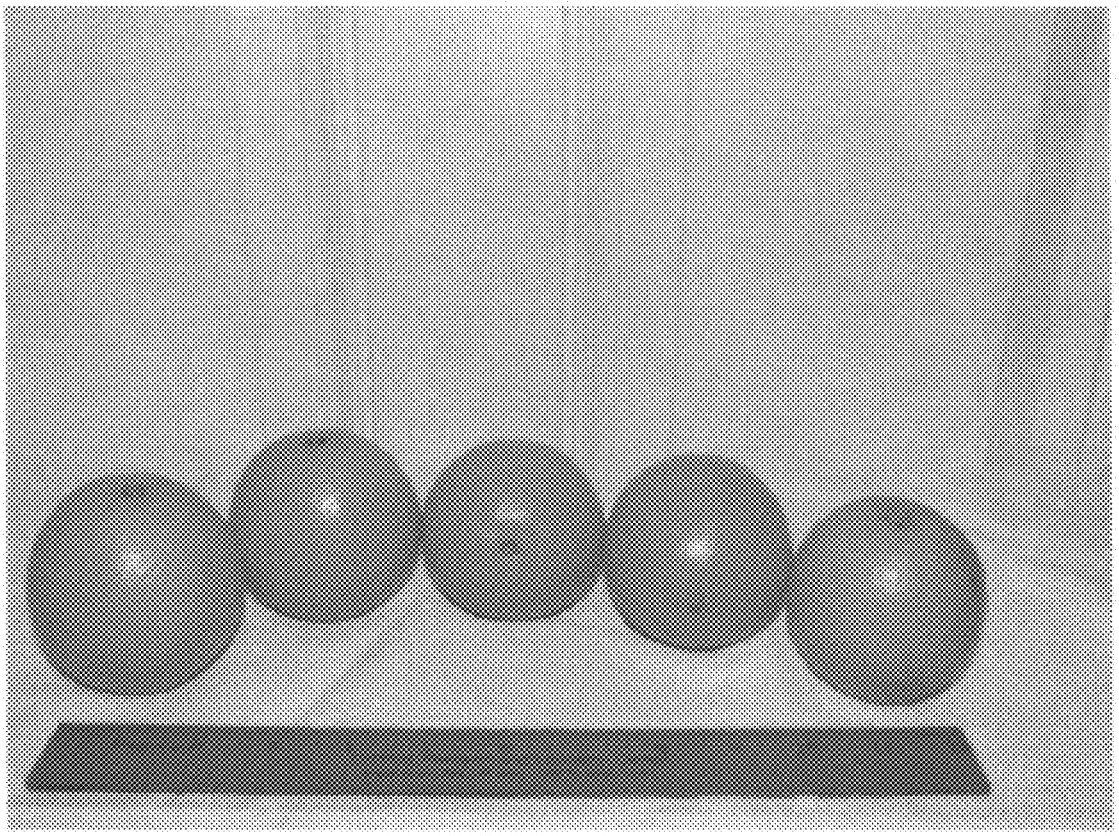
FIG. 5—Shows typical size and color of whole fruit.

Phenotypic Description of *Citrus sinensis* L. Osbeck 'N13-32'

The following detailed description sets forth the distinctive characteristics of 'N13-32'. The present botanical description is that of the variety grown as a 16 year-old tree growing on 'Swingle' rootstock in Lake Alfred, Fla. The colors (except those in common terms) are described from the R. H. S. Colour Chart published by The Royal Horticultural Society in London (second edition), in association with the Flower Council of Holland.

Classification:

*Botanical.*—*Citrus sinensis* L. Osbeck.

*Common name.*—Sweet orange.

Parentage:

*Female parent.*—Somaclonal variant of 'Hamlin' sweet orange (unpatented).

*Male parent.*—N/A.

Tree:

*Ploidy.*—Diploid.

*Size.*—Large.

*Tree height.*—6.0 m.

*Tree spread.*—5.3 to 5.4 m.

*Vigor.*—Vigorous.

*Density.*—Canopies are quite dense.

*Form.*—The tree is obloid shaped with both lateral and upright branches growing; branches with fruit exhibit drooping.

*Growth habit.*—Both upright and lateral growth with medium angle.

Trunk:

*Trunk diameter.*—21 cm in diameter at 30 cm above the ground.

*Trunk texture.*—Smooth.

*Trunk bark color.*—RHS 197A (greyed-green); irregularly striated with RHS 197C (greyed-green).

Branches:

*Crotch angle.*—First crotch forms a 30 to 45-degree angle, the middle crotch forms a 60-degree angle.

*Branch length.*—Branches reach 4.4 meters from the first crotch to the tip of the branch.

*Branch texture.*—Relatively smooth, occasionally with small thorns or spines.

*Branch color* (*shoots from previous flush, hardened, and 4 to 5 mm in diameter*).—RHS N137B (green).

Leaves:

*Size* (*lamina average*).—Length: 122.4 mm. Width: 61 mm. L/W ratio: 2.0.

*Thickness.*—Regular and average compare to commercial 'Hamlin' sweet orange.

*Type.*—Simple.

*Shape.*—Elliptical.

*Apex.*—Slightly retuse, relatively acute.

*Base.*—Acute to sub-obtuse.

*Margin.*—Entire and smooth.

*Surface.*—Upper surface: Glabrous. Lower surface: Medium veins that are pinnately netted.

*Color.*—Upper surface (adaxial): RHS N137A (green). Lower surface (abaxial): RHS 137A (green).

*Petiole.*—Shape: Brevipetiolate (shorter than leaf lamina); junction between petiole and lamina is articulate. Width (petiole wing): Narrow. Shape (petiole wing): Obovate. Length: 2.7 to 3.1 mm. Width: 5.5 to 6.0 mm. Color: RHS N137A (green).

Flowers and flower buds:

*Type.*—Hermaphrodite.

*Bearing.*—Flowers grow from leaf axillaries and leaf terminals in singles and in small clusters; most single flowers grow from leaf axillaries; each flower branch consists of 4-5 flowers.

*Flower diameter.*—Fully open flower has an average diameter of 28 to 32 mm.

*Flower depth.*—Typical flower has an average depth of 17 mm.

*Blooming period.*—First bloom: Observed late March 2012. Full bloom: Observed early April, 2012.

*Flower bud size.*—Length: Initial visible flower bud is 1.8 mm in length; mature flower bud is 19.6 mm in length. Diameter: Initial visible flower bud is 2.1 mm in diameter; mature flower bud is 7.9 mm in diameter.

*Flower bud shape.*—Initial visible flower bud has a round ball shape; mature flower bud has an elongated olive shape.

*Color.*—Initial visible flower Bud: RHS 143 B (green). Mature Flower Bud: RHS NN155A (white) with RHS 1A (green-yellow) spots distributed toward the petal apex.

*Flower petals.*—Number: 5. Length: 17 mm. Width: 7.9 mm. Shape: Flat, spatula shaped. Apex shape: Smooth, acute shaped. Base shape: Even obtuse.

*Color.*—Upper surface: RHS 155B (white). Lower surface: RHS NN155C (white) with RHS 150A (yellow-green) spots distributed toward to the petal apex. Margin: Smooth.

*Sepal.*—Number (per flower): 4 per flower. Shape: Delta shaped with acute angle at apex. Length: 3.6 mm. Width: 3.1 mm. Apex shape: Triangle shaped. Margin: Smooth.

*Color.*—Upper surface: RHS 145D (yellow-green). Lower surface: RHS 145C (yellow-green).

*Fragrance.*—Fragrant.

*Pedicel.*—Number: 1. Length: 4.0 to 5.6 mm. Diameter: 1.2 to 1.6 mm. Color: RHS 142B (green).

*Reproductive organs.*—Fertility: Appears self-fertile. Stamen length: 12.2 to 12.8 mm. Anther. Length: 2.6 mm. Width: 1.1 to 1.2 mm. Color: RHS 13C (yellow). Filament length: 9.2 to 10.0 mm. Pollen amount: Abundant. Pollen color (general): RHS 13A (yellow).

*Pistil.*—Number: 1. Length: 10.6 to 11.0 mm. Color: RHS 145C (yellow-green).

*Style length.*—8.8 mm.

*Style diameter.*—1.1 to 1.6 mm.

*Style color.*—RHS 145C (yellow-green).

*Ovary shape.*—Oval shaped.

*Ovary diameter.*—2.8 mm.

*Ovary color.*—RHS 143C (green).

Fruit:

*Size.*—Uniform.

*Width.*—72 to 74 mm on average.

*Length.*—75 to 76 mm on average.

*Average weight* (*per individual fruit*).—187 g.

*Shape.*—Earth shaped.

*Shape* (*cross-section*).—Round.

*Apex.*—Truncated with shallow dent.

*Apex cavity diameter.*—N/A.

*Base.*—No neck.

*Base cavity diameter.*—7.0 to 7.8 mm.

*Harvesting.*—First pick around December 20 (based on season and rootstock); last pick around March 15, although fruit continue to hold on the tree for a longer time.

*Fruit stem* (*short stem connecting the fruit*).—Length: 9.0 mm. Diameter: 3.8 mm. Color: RHS 137A (green) with RHS 197C (greyed-green) strip.

Skin:

*Adherence.*—Adherence between albedo (mesocarp) and flesh (endocarp) is strong, similar to commercial 'Hamlin' sweet orange; the adherence is evenly distributed from base to apex.

*Thickness.*—3.5 to 4.5 mm on average.

*Texture.*—Smooth.

*Color.*—Flavedo (epicarp): Ranges between RHS 15A (yellow-orange) to RHS 16A (yellow-orange). Albedo (mesocarp): RHS 18C (yellow-orange). Stylar end: Closed.

*Rind oil cell density.*—120-136 oil cells/square cm.

Flesh:

*Number of segments.*—Averages between 10 and 11 segments per fruit.

*Segment walls.*—Medium soft with sufficient strength to maintain integrity as separated.

*Juice.*—Abundant.

*Color.*—Uniformly RHS 16A (yellow-orange).

*Texture.*—Medium soft.

*Vesicles.*—Length: arranged from 16 to 17.6 mm on average. Diameter (thickness): 3.5 to 4.2 mm on average.

*Eating quality* (*tested at the beginning of March*), *varies from season to season.*—Soluble solids (average): 10.4-11.4. Acidity (average): 0.6-0.7%. Sugar/Acid Ratio : 16-18.5. Juice Color Index : 34.0-36.7.

Seeds:

*Type.*—Polyembryonic.

*Number.*—Ranges from 2 to 11; highly variable.

*Shape.*—Seed shapes are not uniform. Normal seeds are mostly ventricose/swollen shaped and clavate, club shaped.

*Size.*—Length: 14 to 15.8 mm. Width: 8.5 to 10.5 mm.

*Seed coat color.*—Outer Surface: RHS NN155D (white) and smooth. Inner surface: RHS 165C (greyed-orange).

*Cotyledon color.*—RHS 155A (white).

Resistance to disease: The original tree is showing better tolerance to HLB than adjacent 'Hamlin' somaclones. Otherwise, disease resistance is typical of 'Hamlin' sweet orange.

What is claimed is:

1. A new and distinct cultivar of sweet orange tree as illustrated and described herein.

* * * * *